US009516407B2

(12) United States Patent
Goldstein et al.

(10) Patent No.: US 9,516,407 B2
(45) Date of Patent: Dec. 6, 2016

(54) ACTIVE NOISE CONTROL WITH COMPENSATION FOR ERROR SENSING AT THE EARDRUM

(71) Applicant: Apple Inc., Cupertino, CA (US)

(72) Inventors: Andre L. Goldstein, San Jose, CA (US); Yacine Azmi, San Francisco, CA (US); Esge B. Andersen, Campbell, CA (US)

(73) Assignee: Apple Inc., Cupertino, CA (US)

( * ) Notice: Subject to any disclaimer, the term of this patent is extended or adjusted under 35 U.S.C. 154(b) by 372 days.

(21) Appl. No.: 13/965,767

(22) Filed: Aug. 13, 2013

(65) Prior Publication Data

US 2014/0044275 A1 Feb. 13, 2014

Related U.S. Application Data

(60) Provisional application No. 61/682,689, filed on Aug. 13, 2012.

(51) Int. Cl.

| | |
|---|---|
| ***H04R 3/00*** | (2006.01) |
| ***H04R 3/02*** | (2006.01) |
| ***G10K 11/16*** | (2006.01) |
| ***H03B 29/00*** | (2006.01) |
| ***A61F 11/06*** | (2006.01) |
| ***H04R 1/10*** | (2006.01) |

(52) U.S. Cl.

CPC ............ *H04R 3/002* (2013.01); *H04R 1/1083* (2013.01); *H04R 3/005* (2013.01); *H04R 3/02* (2013.01); *H04R 2410/05* (2013.01); *H04R 2420/07* (2013.01)

(58) Field of Classification Search

USPC .......................................................... 381/71.6

See application file for complete search history.

(56) References Cited

U.S. PATENT DOCUMENTS

| | | | | |
|---|---|---|---|---|
| 6,160,893 | A | 12/2000 | Saunders et al. | |
| 6,741,707 | B2 | 5/2004 | Ray et al. | |
| 2006/0069556 | A1* | 3/2006 | Nadjar ................. | G10K 11/178 704/229 |
| 2009/0080670 | A1* | 3/2009 | Solbeck ............... | H04R 25/453 381/71.6 |
| 2011/0299695 | A1 | 12/2011 | Nicholson | |
| 2012/0140917 | A1* | 6/2012 | Nicholson .......... | G10K 11/1782 379/392.01 |
| 2012/0151394 | A1* | 6/2012 | Locke ................ | G06F 3/04817 715/765 |
| 2013/0058493 | A1 | 3/2013 | Darlington | |
| 2013/0094657 | A1 | 4/2013 | Brammer et al. | |
| 2013/0274628 | A1* | 10/2013 | Fausti .................... | A61B 5/123 600/559 |

OTHER PUBLICATIONS

Kuo et al., "Active Noise Control System for Headphone Application", Mar. 2, 2006, IEEE http://ieeexplore.ieee.org/stamp/stamp.jsp?arnumber=1597204.*

(Continued)

*Primary Examiner* — Duc Nguyen
*Assistant Examiner* — Yogeshkumar Patel
(74) *Attorney, Agent, or Firm* — Blakely, Sokoloff, Taylor & Zafman LLP

(57) ABSTRACT

A personal listening system has an active noise control (ANC) controller that produces an anti-noise signal. A head worn audio device for a user has a speaker to convert the anti-noise signal into anti-noise, an error microphone, and a reference microphone. The controller uses signals from the error and reference microphones to produce the anti-noise signal in accordance with an adaptive filter algorithm that has an adjustable parameter which changes so as to move the point at which acoustic cancellation occurs from the error microphone and closer to the user's eardrum. Other embodiments are also described and claimed.

24 Claims, 11 Drawing Sheets

(56) References Cited

OTHER PUBLICATIONS

Audio-Technica ATH-ANC9 QuietPoint® Instruction Manual, Noise-Cancelling Headphones, May 30, 2012, (40 pages).

Benoit, Michael, et al., "Engineering Silence: Active Noise Cancellation", Jul. 10, 2011, Internet download at: http://www.docstoc.com/docs/84232331/Engineering-Silence-Active-Noise-Cancellation, (12 pages).

Burkhard, M. D., "Measuring the Constants of Ear Simulators", Journal of the Audio Engineering Society, Dec. 1977, vol. 25, No. 12, pp. 1008-1015.

Kuo, Sen M., "Active Noise Control System for Headphone Applications", IEEE Transactions on Control Systems Technology, vol. 14, No. 2, Mar. 2006, (pp. 331-335).

Kuo, Sen M., et al., "Active Noise Control Systems with Optimized Secondary Path", Control Applications, 2004, Proceedings of the IEEE International Conference, (vol. 1), Sep. 2-4, 2004, ISBN: 0-7803-8633-7, (8 pages).

Kuo, Sen M., et al., "Design of Active Noise Control Systems with the TMS320 Family", Application Report, Texas Instruments, Digital Signal Processing Solutions, Digital Signal Processing Products—Semiconductor Group, SPRA042, Jun. 1996, (171 pages).

Moreau, Danielle, et al., "A Review of Virtual Sensing Algorithms for Active Noise Control", Algorithms, 2008, 1, 69-99; DOI: 10.3390/a1020069, ISSN 1999-4893, www.mdpi.com/journal/algorithms, (pp. 69-99).

Munn, Jacqueline M., "Virtual Sensors for Active Noise Control", Department of Mechanical Engineering, The University of Adelaide, South Australia, Printed May 13, 2004—Submitted for the degree of Ph.D. in Mechanical Engineering on Jul. 17, 2003—Awarded Oct. 27, 2003, (284 pages).

Struck, Christopher J., "Electroacoustic Measurements of Headphones", CJS Labs, San Francisco, CA—USA, Dec. 2009, (13 pages).

Veloso, Alex J., et al., "Headphone with Active Noise Control Using Analog Adaptive Filters", inter-noise Environmental Noise Control, The 2005 Congress and Exposition on Noise Control Engineering, Aug. 7-10, 2005, Rio de Janeiro, Brazil, (8 pages).

* cited by examiner

ACTIVE NOISE CONTROL WITH COMPENSATION FOR ERROR SENSING AT THE EARDRUM

RELATED MATTERS

This application claims the benefit of the earlier filing date of provisional application No. 61/682,689, filed Aug. 13, 2012, entitled "Active Noise Control with Compensation for Error Sensing at the Ear Drum".

BACKGROUND

Active noise control (ANC) is a technique that aims to "cancel" unwanted noise, by introducing an additional, electronically controlled sound field, also referred to as anti-noise. The anti-noise is electronically designed so as to have the proper pressure, amplitude and phase, that destructively interferes with the unwanted noise, as detected by an error sensor (typically an error microphone). With recent advances in digital signal processing, the application of active noise control specifically to personal consumer electronics listening devices, such as smart phones and headphones, is becoming more practical. Improvements in the performance of ANC are welcome.

SUMMARY

The same sound produced by a headphone, such as for example an ear fitting headphone or ear bud, is experienced differently by different users, due in part to the way in which the headphone is worn or carried by each user's ear. In addition, the volume of the ear canal, as well as its shape and/or length, together with movement of the headphone (due to the user, for example, moving her head while walking or jogging) are additional factors that cause the listening experience to vary between users of the same headphone design. In other words, the frequency response of the overall sound producing system, which includes the electro-acoustic response of the headphone and the physical or acoustic features of the user's ear up to the eardrum, can vary substantially during normal end-user operation, as well as across different users. Now, this may impact the effectiveness of an active noise control (ANC) mechanism that aims to reduce the ambient noise that is being heard by the wearer of the headphone. This may be because the "error" signal that is picked up by the error microphone, and is used by the ANC mechanism to adjust the anti-noise, is not actually located at the eardrum where the user is actually experiencing the results of the anti-noise and the unwanted ambient noise coming together. Rather, the error microphone may be located within the audio device housing just in front of the headphone speaker driver. Also, with certain types of head worn audio devices, such as loose fitting ear buds, there is significant acoustic leakage between the atmosphere or ambient environment and the ear canal, past the external surfaces of the audio device housing and the ear. This acoustic leakage may be due to the loose fitting nature of the audio device, which promotes comfort for the user. However, the additional acoustic leakage does not allow for enough passive attenuation of the ambient noise at the user's eardrum, and so the ANC mechanism may be effective in such circumstances.

In accordance with an embodiment of the invention, additional signal processing is performed so as to in effect estimate the effect of the gap within the user's ear canal that lies between the error microphone (as it is located for example in a headphone housing) and the eardrum. Based on that estimate, the ANC controller is compensated, so that the noise cancellation may be effectively optimized at the eardrum, rather than at the error microphone. This may be viewed as implementing a "virtual" error sensor that would be located at the eardrum. Several techniques for doing so are described below and which exhibit improved ANC performance, i.e. they yield increased noise cancellation within certain audio frequency bands.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

DETAILED DESCRIPTION

Several embodiments of the invention with reference to the appended drawings are now explained. While numerous details are set forth, it is understood that some embodiments of the invention may be practiced without these details. In other instances, well-known circuits, structures, and techniques have not been shown in detail so as not to obscure the understanding of this description.

Figure 1:
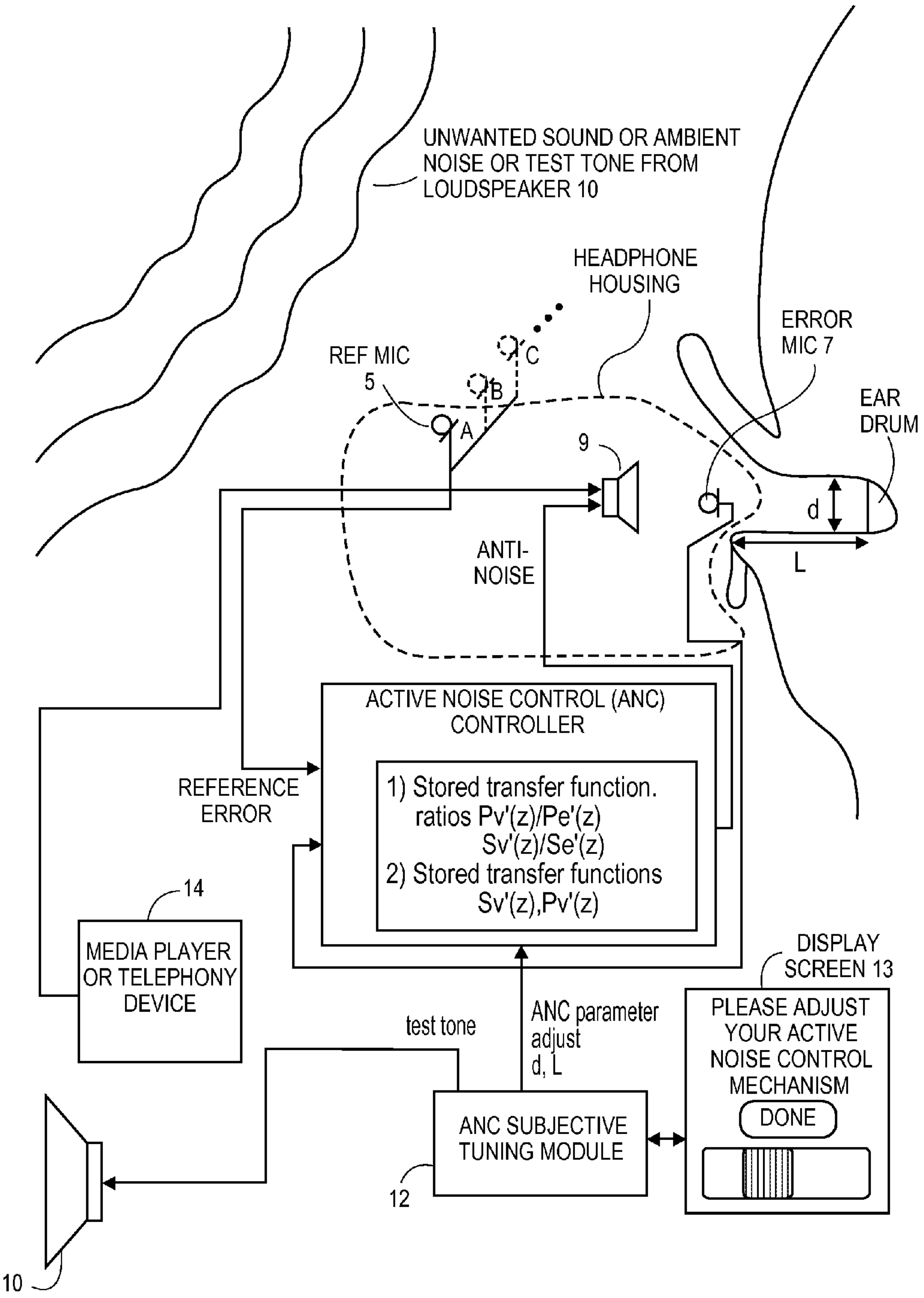
FIG. 1 is a block diagram of a consumer electronics listening system that features an ANC controller having an adjustable parameter for improving the user's listening experience.

An embodiment of the invention is an ANC mechanism that is implemented in a personal listening system that uses a wired headphone, a smartphone handset, a wireless headset, or other head worn audio device. FIG. 1 is a block diagram of such a consumer electronics listening system. The listening system depicted in this example includes a head worn audio device that is "worn" by the user in that it's speaker is closely positioned next to the user's ear. The device housing contains an earpiece speaker driver 9, and an error microphone 7 that is located in front of the driver 9.

Figure 2:
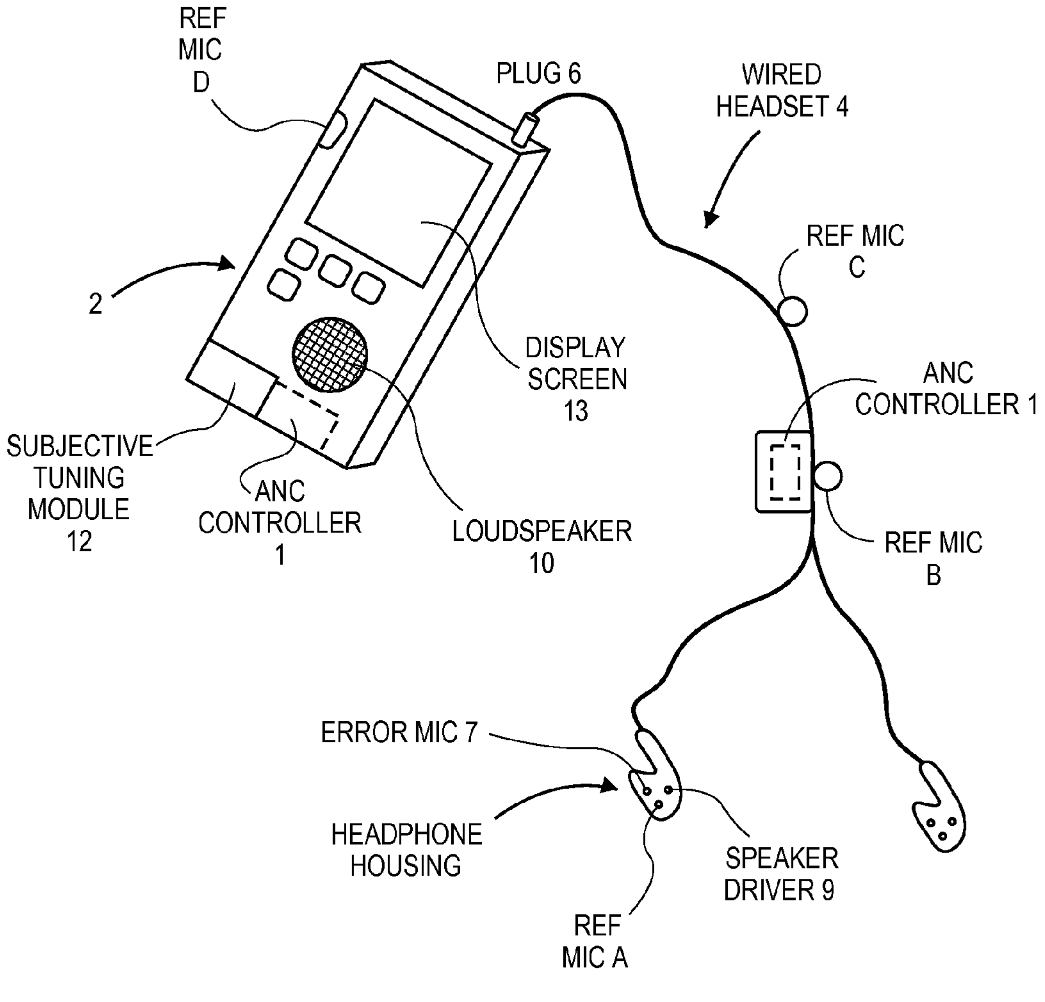
FIG. 2 illustrates an example personal listening device in which an ANC controller and subjective tuning module can be implemented.

The head worn audio device may be coupled to the audio signal source through a wireless communication link, e.g. a wireless Bluetooth headset. Alternatively, the head worn audio device is a wired headset. In that case, the device housing may that of a headphone such as a loosely fitting earbud as shown in FIG. 2, or alternatively a sealed in-ear earphone. The speaker driver 9 may be part of a wired headset 4 as depicted in FIG. 2, which receives both power and an audio content signal from a connected host or source device 2, such as a portable personal audio or multi-function device (e.g., a smartphone, a tablet computer, or a compact digital audio player).

Figure 3:
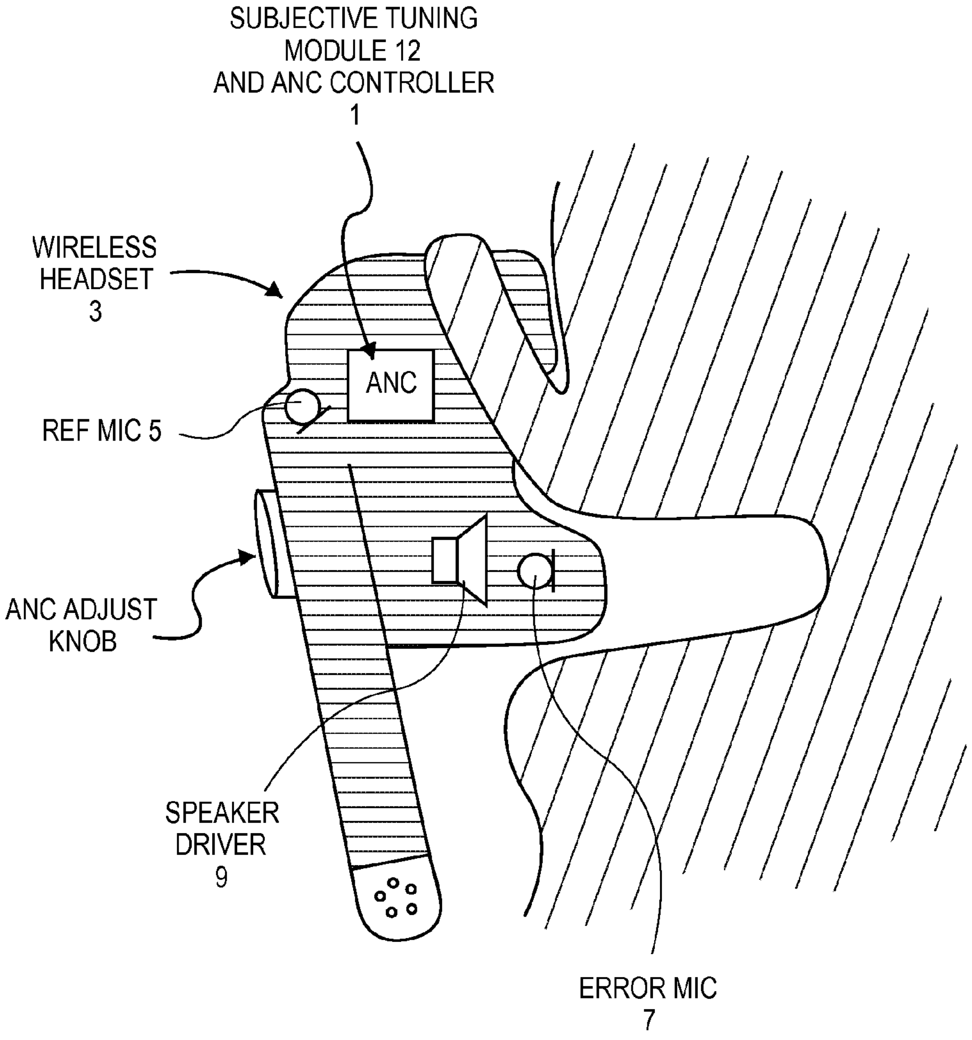
FIG. 3 depicts another personal listening device, namely a wireless headset.

As an alternative, the speaker driver 9 and the error microphone 7 may be part of a wireless headset 3 (e.g., a Bluetooth compatible wireless headset) as shown in FIG. 3. As a further alternative, the speaker driver 9 and the error mic 7 may be in the receiver (earpiece) portion of the housing of a smartphone handset (that is "worn" by being held against the user's ear). In most of these cases, there is appreciable acoustic leakage past the device headphone or earpiece housing and into the ear canal, of unwanted sound or ambient noise in the atmosphere. Such acoustic leakage also tends to lower the acoustic impedance seen by the speaker driver 9, as compared to a sealed over the ear or a sealed insert-type earphone.

The audio device housing may also include a reference microphone 5 (ref mic A) that may be located behind the speaker driver 9 as shown. There may be one or more such reference microphones that serve to pick up the ambient noise (for processing as a reference signal by the ANC mechanism). For example, ref mics B and C are positioned on the headset cable (in FIG. 2) that has at one end a headphone housing and at another end a tip ring sleeve (TRRS) connector or plug 6. There may also be a further ref mic D that is located in the housing of the source device as shown. Note here that the error and reference microphones may each be one or more acoustic microphones or sound pickup devices, in that there may be multiple audio pickup devices whose signals are combined into a single reference or error signal, using for example beamforming and/or other audio signal processing.

Signals from the ref mic 5 and error mic 7 are digitized and processed by an active noise control (ANC) controller 1 (that may or may not be integrated within the audio device housing). The ANC controller 1, which may be implemented in the form of hardwired logic circuitry or as a programmed processor that implements digital audio processing operations upon the reference and error signals, could be implemented inside the earphone housing of a wired headset as in FIG. 2 or inside a wireless headset housing as in FIG. 3. It could alternatively be implemented outside of the headphone housing, for example, within a case that is attached to an intermediate location along the cable of a wired headset 4—see FIG. 2. Digitized ref mic signals can be routed to the ANC controller through different means, including for example via the headset cable as shown in FIG. 2. Alternatively, the ANC controller 1 may be implemented in the form of a programmable processor located inside the source device 2 housing.

The ANC controller 1 produces an anti-noise signal that in this embodiment is driven through the same speaker driver 9 that also receives the desired audio content from a media player or a telephony device 14. Additional signal processing components (not shown) may be needed to isolate the residual unwanted noise or ANC error from the desired audio content (because both would be contained in the error mic signal). The ANC controller 1 operates while the user is for example listening to a digital music file that is stored in or is being streamed into the source device 2 (e.g., a portable personal audio or multifunction device as depicted in FIG. 2). Alternatively, the ANC operates while the user is conducting a conversation with a far-end user of a communications network in an audio phone call or a videophone call.

Figure 4:
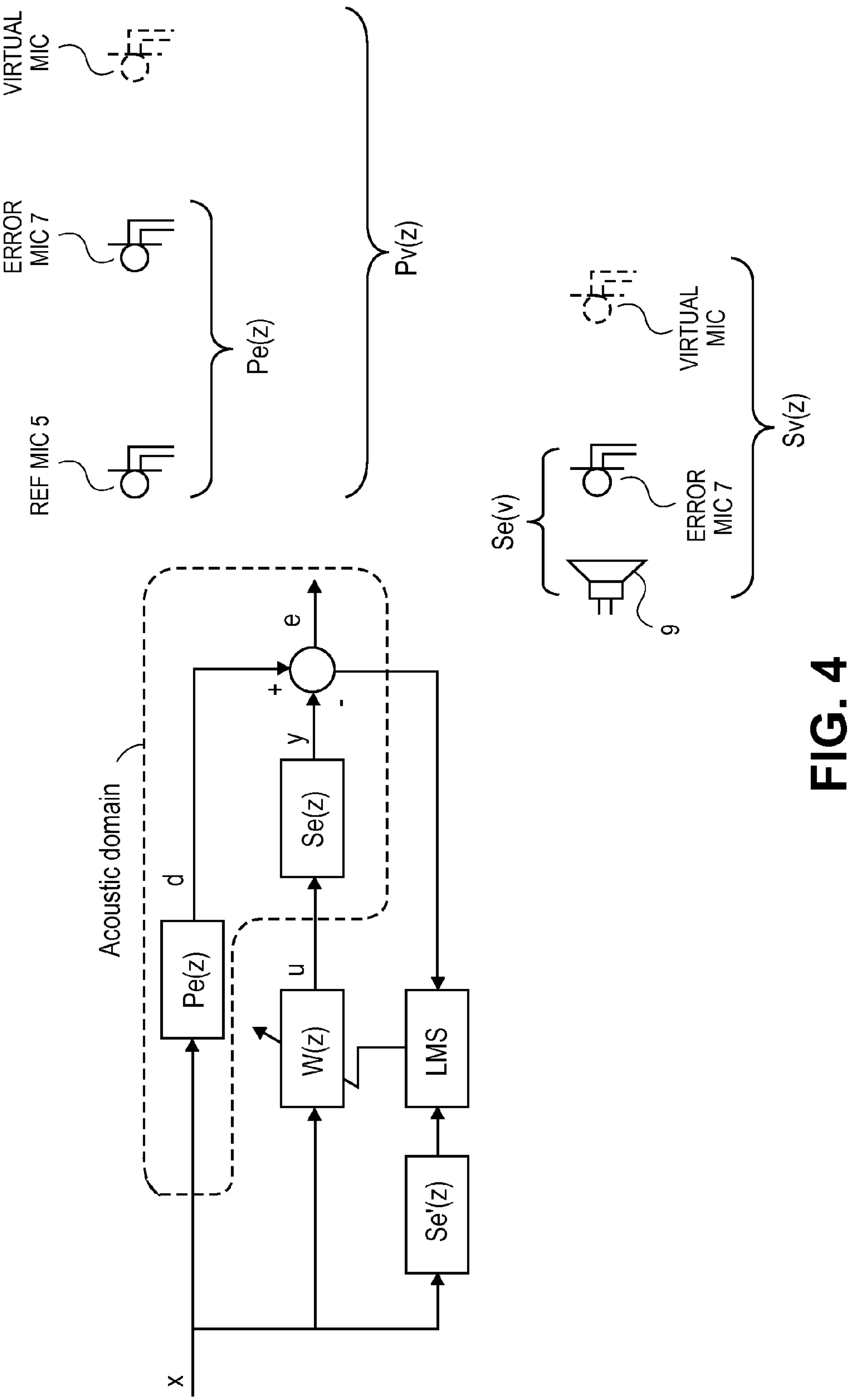
FIG. 4 is a block diagram of a conventional filtered-x LMS feed forward ANC system or algorithm, together with definitions of primary and secondary virtual error sensing transfer functions.

The ANC controller 1 may implement a conventional feed forward, feed back, or hybrid noise control algorithm. FIG. 4 shows as an example a filtered-x least mean squares (LMS) feed forward version. The controller operates with an acoustic domain being represented by Pe(z), which represents a primary acoustic path for the disturbance x arriving at an error sensor (error mic 7) as disturbance d, which is combined acoustically (in the user's ear canal) with an anti-noise y in a destructive manner, to result in a residual noise or error, e. The error microphone 7 serves to pickup this residual noise or error, in addition to any user audio content that is being also heard by the user. The performance of the ANC controller will be monitored by an adaptive filter controller, using the signal from the error microphone 7.

The primary path taken by the disturbance or noise between a reference microphone 5 and the error microphone 7 is represented by the transfer function Pe(z), while Se represents the secondary path between a speaker driver 9 and the error microphone 7. An anti-noise signal u is produced by a W-filter, which is in this embodiment a feed forward adaptive digital filter that is adapted by an adaptive filter controller, in this example according to an LMS algorithm. Other adaptive filter algorithms can be used, including ones that use different adaptive filter controllers. Note that d represents the acoustic disturbance or unwanted noise that arrives at the error sensor (or error mic 7), while y is the acoustic anti-noise at the error sensor. x represents the reference or acoustic ambient noise. The latter may be assumed to be properly picked up by the reference microphone 5.

The LMS controller adjusts the coefficients of the digital filter W(z) in order to adapt to the changing error, e. In doing so, the LMS controller also uses a digitally filtered version of the reference x, i.e. filtered in accordance with Se'(z), which is a model or estimate of the actual secondary transfer function Se(z). Now, Se'(z) may be determined according to techniques known to those of ordinary skill in the art, either as a fixed digital filter determined offline, or as an adaptive filter that is adapted online (using another adaptive filter algorithm, not shown), i.e. while the user is wearing the head worn device and the personal listening system is converting user audio content (e.g., during a voice or video telephony call or during a one-way digital media streaming or playback session). In one embodiment, the LMS controller adjusts W(z) based on the instantaneous gradient of a single squared error sample, and upon convergence where we assume that the error is equal to zero, Woptimal(z)=Pe(z)/Se(z). To verify this, looking at the block diagram of FIG. 4, it can be seen that E(z)=[Pe(z)−Se(z)*W(z)]*X(z) such that making E(z)=0 results in Wopt(z)=Pe(z)/S(e). Accordingly, upon convergence, knowledge of W(z) yields the ratio Pe'(z)/Se'(z).

Referring back to FIG. 1, it can be seen that the error microphone 7 is located at a gap or distance from the eardrum of the user, approximately represented by the distance of the ear canal, L. The ear canal also has an approximate diameter, d. In the case where the error microphone 7 is packaged within a headphone housing, such as a loose fitting in-ear earphone, or where the error microphone 7 is located in the housing of a receiver or earpiece speaker of a cellular phone handset, there is an appreciable gap between the location of the error microphone 7 and the eardrum. In other words, while noise cancellation is attempted at the error sensor location, it would be desirable to compensate or change the behavior of the ANC controller so that the noise cancellation would occur at the eardrum where the user is actually hearing the beneficial impact of the anti-noise canceling the unwanted noise. This technique is referred to as "virtual" error sensing, in that it is not possible to physically locate an error sensor at the eardrum. Referring to FIG. 4, this means that in addition to the conventional transfer function Pe(z), there is now another primary path transfer function Pv(z), which represents the primary path taken by the disturbance d between the reference microphone 5 and a virtual microphone or virtual sensor location. Similarly, the adaptive filter algorithm now also needs to consider a secondary path transfer function Sv(z) between the speaker 9 and the virtual microphone location. Given that, as explained above in connection with the LMS controller, Pe'(z) and Se'(z) are essentially "known" entities, the problem for the adaptive filter algorithm while operating in "virtual error sensing mode" becomes how to determine the unknown entities of Sv'(z) and Pv'(z), which are the estimates of the respective transfer functions to the virtual sensor location.

Figure 5:
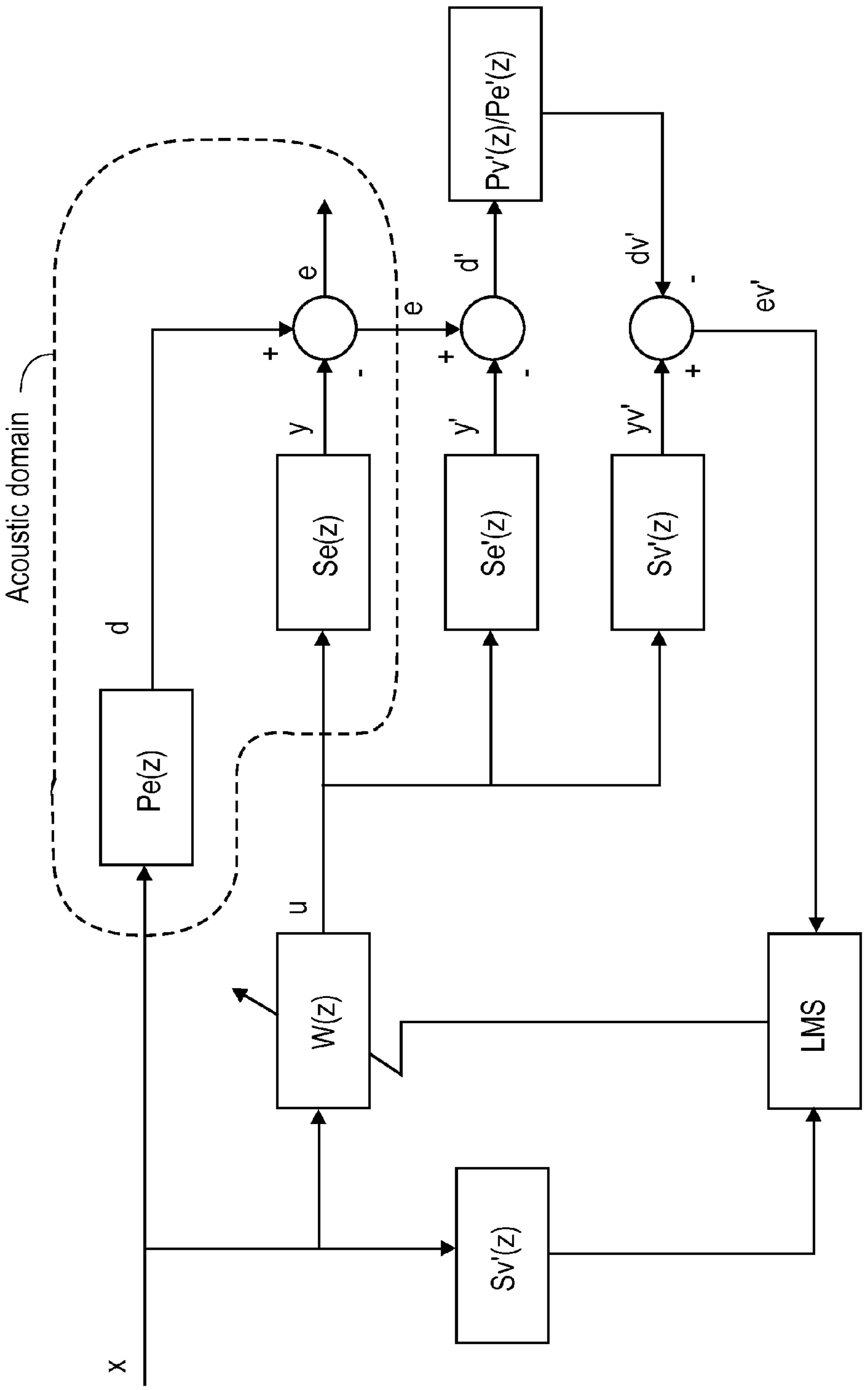
FIG. 5 shows how the conventional ANC algorithm of FIG. 4 can be modified to provide compensation for virtual error sensing at the eardrum.

Turning now to FIG. 5, FIG. 5 shows a modification to the conventional ANC system of FIG. 4 that allows virtual error sensing. The controller still produces an anti-noise signal u but in the context of a virtual error sensing mode of operation. The adaptive filter algorithm in this case operates based on the following transfer functions which are models or estimates of their respective acoustic and electronic paths introduced above in connection with FIG. 4, namely Se'(z), Pe'(z), Sv'(z), and Se'(z). These are primary and secondary path transfer functions to an actual error sensor (Pe'(z) and Se'(z)) and primary and secondary path transfer functions which model the primary disturbance path and secondary path to a virtual error sensor (Pv'(z) and Sv'(z)).

As in FIG. 4, d is the primary disturbance in the acoustic domain, y is the anti-noise in the acoustic domain, and e is the residual noise or error at the actual error microphone. The components outside the acoustic domain may be deemed part of the ANC controller 1, which can be implemented as a digital signal processor that operates on line, which is while the controller is operational and is producing anti-noise that can be heard by the user who is wearing the personal listening system.

Additional variables depicted in FIG. 5 that are relevant to the virtual error sensing mode of operation include y' which is the estimated anti-noise that is obtained as a result of having filtered the anti-noise signal u in accordance with Se'(z). The signal produced by the actual error sensor or error microphone 7 is also represented in this case as e, from which the estimated anti-noise y' is subtracted, in order to yield an estimate of the disturbance at the actual error sensor. The latter is then filtered in accordance with a transfer function Cvm(z) where in this case it has been assumed that Cvm(z)=Pv'(z)/Pe'(z). This ratio of Pv'(z) to Pe'(z) effectively estimates the transfer function between sound pressure at the virtual microphone (user ear drum) location and the error microphone 7. Cvm(z) can be computed using the transfer function or acoustic impedance of the user's ear canal (see FIG. 1). The result is dv' which is the predicted disturbance at the virtual error sensor location. Now, in order to obtain the desired ev', which is the estimated residual noise or error signal at the virtual sensor location, dv' is subtracted from yv', where yv' is the predicted signal that would be produced by a virtual error sensor, or otherwise known as the acoustic pickup at the virtual error sensor location. Here, yv' is obtained by filtering the anti-noise signal u in accordance with Sv'(z). In effect therefore, a prediction regarding cancellation at the virtual error sensor is made, in the form of ev'. It is this error signal that is now fed to the adaptive W-filter controller (here, LMS controller). Compare this to the conventional approach for operating the adaptive filter algorithm based on just an actual error sensor (depicted in FIG. 4).

One further difference between the adaptive filter algorithm of FIG. 5 and that of FIG. 4 is the need for obtaining a "filtered-x" signal which is a filtered version of the reference or disturbance x, in accordance with Sv'(z), rather than Se'(z). A further modification may be made in this case, referring now to FIG. 6, by assuming that Cvm(z), which is essentially equal to the ratio Pv'(z)/Pe'(z), is also equal to the ratio Sv'(z)/Se'(z). This is a reasonably good assumption, for example, up to a certain frequency, e.g. about 10 kHz. With that assumption, referring now to FIG. 6, Sv'(z)=Se'(z)×Cvm(z), where this change can be reflected in the diagram of FIG. 5 whenever Sv'(z) is needed. Coming back to FIG. 6, the unknown entity at this point becomes Cvm(z)=Pv'(z)/Pe'(z)=Sv'(z)/Se'(z).

Figure 6:
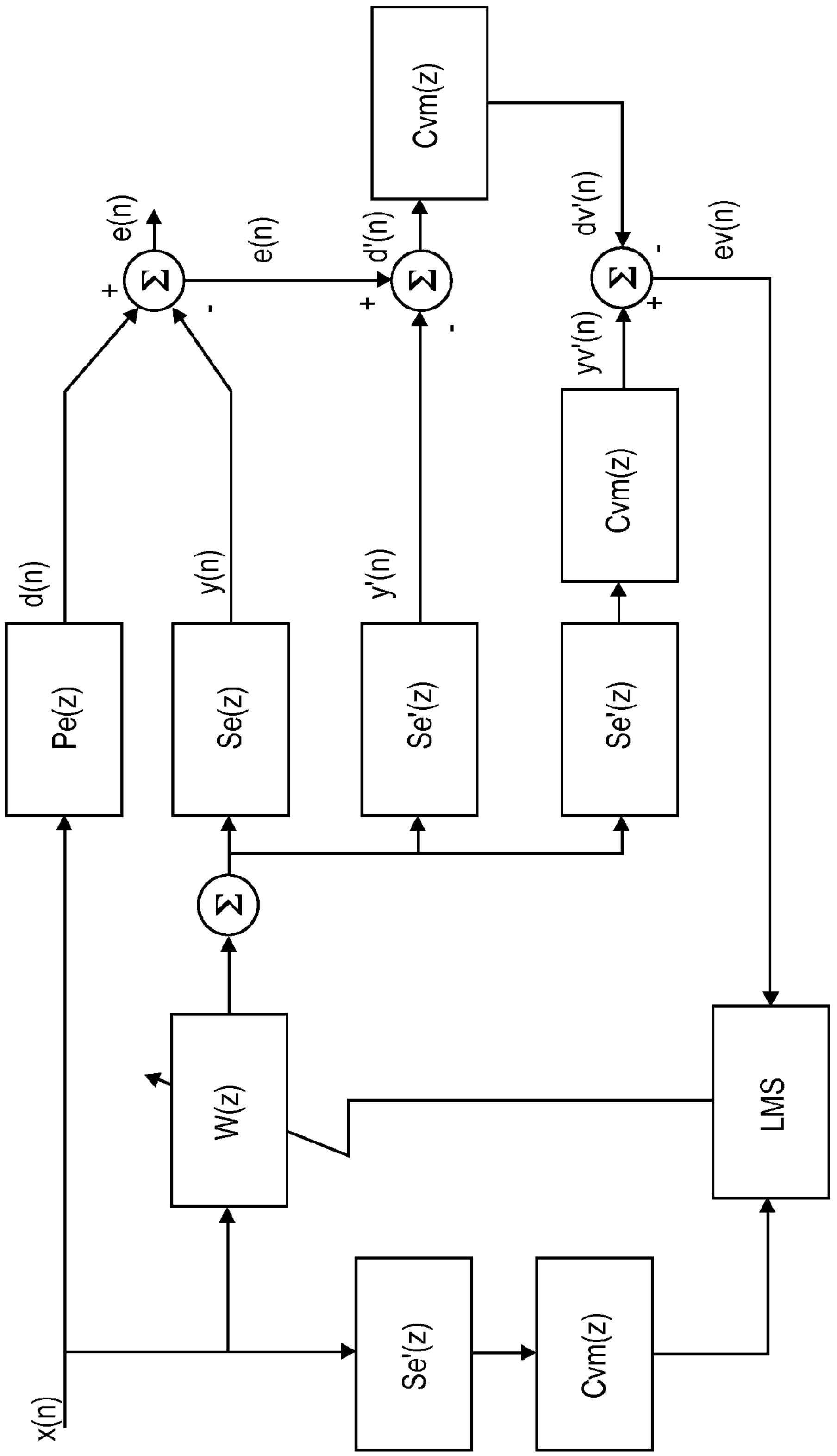
FIG. 6 shows another virtual error sensing modification to the conventional ANC system of FIG. 4.
Figure 7:
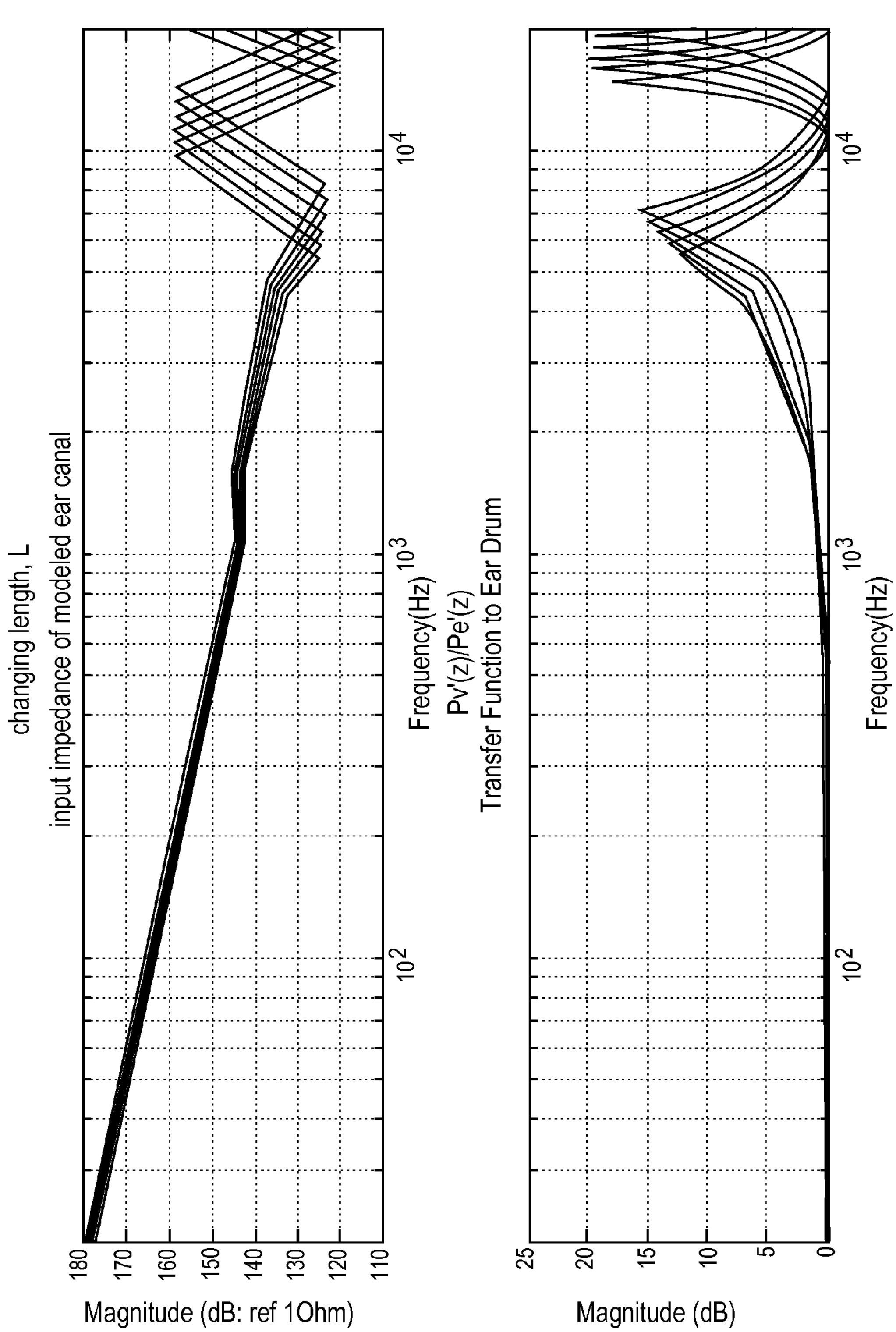
FIG. 7 shows input acoustic impedance curves for a modeled ear canal and associated transfer functions to the eardrum, as a function of changing length of the ear canal.

To deal with the impossibility of placing a real error sensor at the user's eardrum (towards measuring the unknown Cvm(z)), the ANC controller 1 of FIG. 5 or FIG. 6 can be implemented as follows. A baseline or generic version of the transfer function Cvm(z) is measured and/or computed "off-line", i.e. in a laboratory setting. For example, a mannequin-based ear simulator that models an "average" ear canal having a length L and a diameter d can be used, to obtain a statistical best fit transfer function Pv'(z)/Pe'(z) for actual measurements of Pv'(z) and Pe'(z) that are obtained from several manufactured specimens of the headphone (see FIG. 1) that are fitted to the mannequin-based ear simulator. Alternatively, Cvm(z) can be computed directly using mathematical relationships that are based on measurements of an average ear canal's acoustic input impedance. The average (or otherwise statistically relevant) model or measurement may be obtained from studies that have been performed upon a number of different human ears. The generic Cvm(z) is then stored in the ANC controller 1.

In addition to the baseline or generic version of Cvm(z), an adjustment range is determined for the ear canal parameters L and d, that covers most of the variation in expected human ears (those who will be wearing the personal listening system of which the ANC controller 1 will be a part). A mathematical relationship or formula between Cvm(z) and the ear canal parameters is determined and stored in the ANC controller 1. Alternatively, a lookup table may be determined that gives a number of computed and/or measured Cvm(z) and their respective sets of ear canal parameters. In both instances, the ANC controller 1 can now determine a new version of Cvm(z) "online", i.e. during in-the-field use of the personal listening system, based on a given set of ANC parameters. The approach will be how to find, online, the set of ANC parameters (e.g., ear canal length L and diameter d) that are sufficiently close to the ear canal characteristics of the user who is using or wearing the listening system. This solution is then expected to provide enhanced ANC noise reduction in the context of that particular user.

In one embodiment, the controller adjusts Cvm(z), in an online process, in accordance with manual input from, or selected by, the user who is wearing the personal listening system. This manual input will then represent the user's listening experience of the anti-noise signal and the disturbance, while the controller is operating in the virtual error sensing mode and has been updated with a new version of Cvm(z) that is in accordance with the ANC parameters that correspond to the manual input selected by the user. Referring back to FIG. 1, each time there is a change in the manual input from the user, an ANC subjective tuning module 12 captures such a change and on that basis adjusts one or more ANC parameters (e.g., ear canal parameters L, d) in accordance with the changed user input. This adjustment to the ANC parameters is then applied by the ANC controller 1 to change the Cvm(z) transfer function, as per a previously determined math relationship or a lookup table that is stored in the ANC controller.

Figure 8:
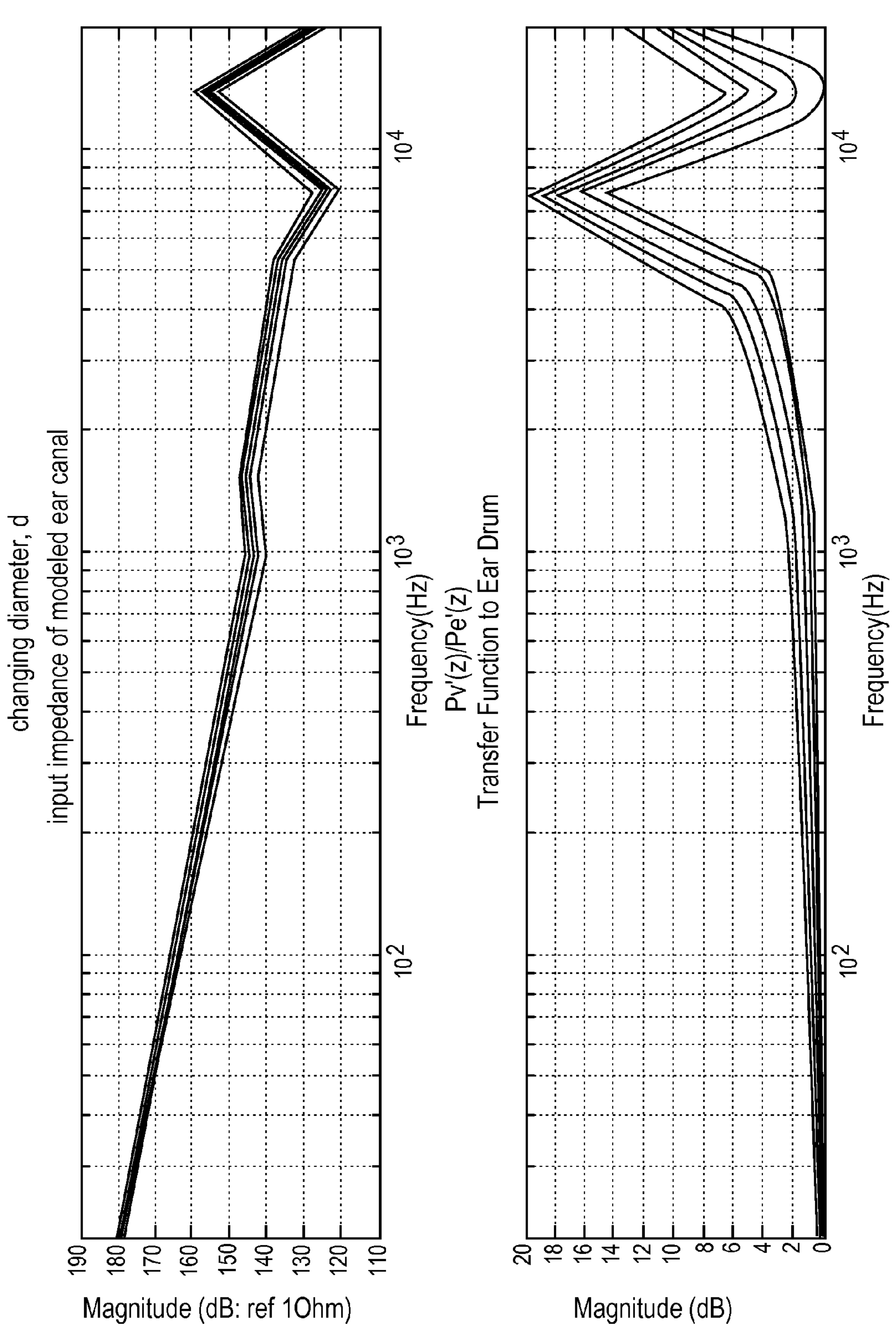
FIG. 8 shows curves for input impedance of the modeled ear canal and associated transfer functions to the eardrum, as a function of changing diameter of the modeled ear canal.

The change to Cvm(z) may be effected within Sv'(z), Pv'(z), the ratio Pv'(z)/Pe'(z), or the ratio Sv'(z)/Se'(z). In a laboratory setting, a relationship between ear canal parameters L and d and ear acoustic input impedance or ear canal input impedance can be derived. A corresponding Cvm(z) can then be determined based on a given ear canal impedance. This allows Cvm(z) to be determined for a given set of ANC parameters L, and d. The results of such laboratory testing for a particular example are given by the curves depicted in FIG. 8 and FIG. 9. In FIG. 8, the input impedance of a modeled ear canal is shown, which may be either computed using an appropriate ear model or measured from a physical mannequin, as a function of changing length, L. Next, using a derived mathematical expression for Cvm(z), which relies on the measured or computed ear canal impedance curve, a corresponding set of curves for the transfer function Pv'(z)/Pe'(z) to the eardrum can be derived. These are depicted by an example in the lower graph of FIG. 8. Although only magnitude v. frequency curves are shown, it should be understood that phase v. frequency curves are also needed for characterizing Cvm(z) and that can be readily computed using similar techniques.

Figure 9:
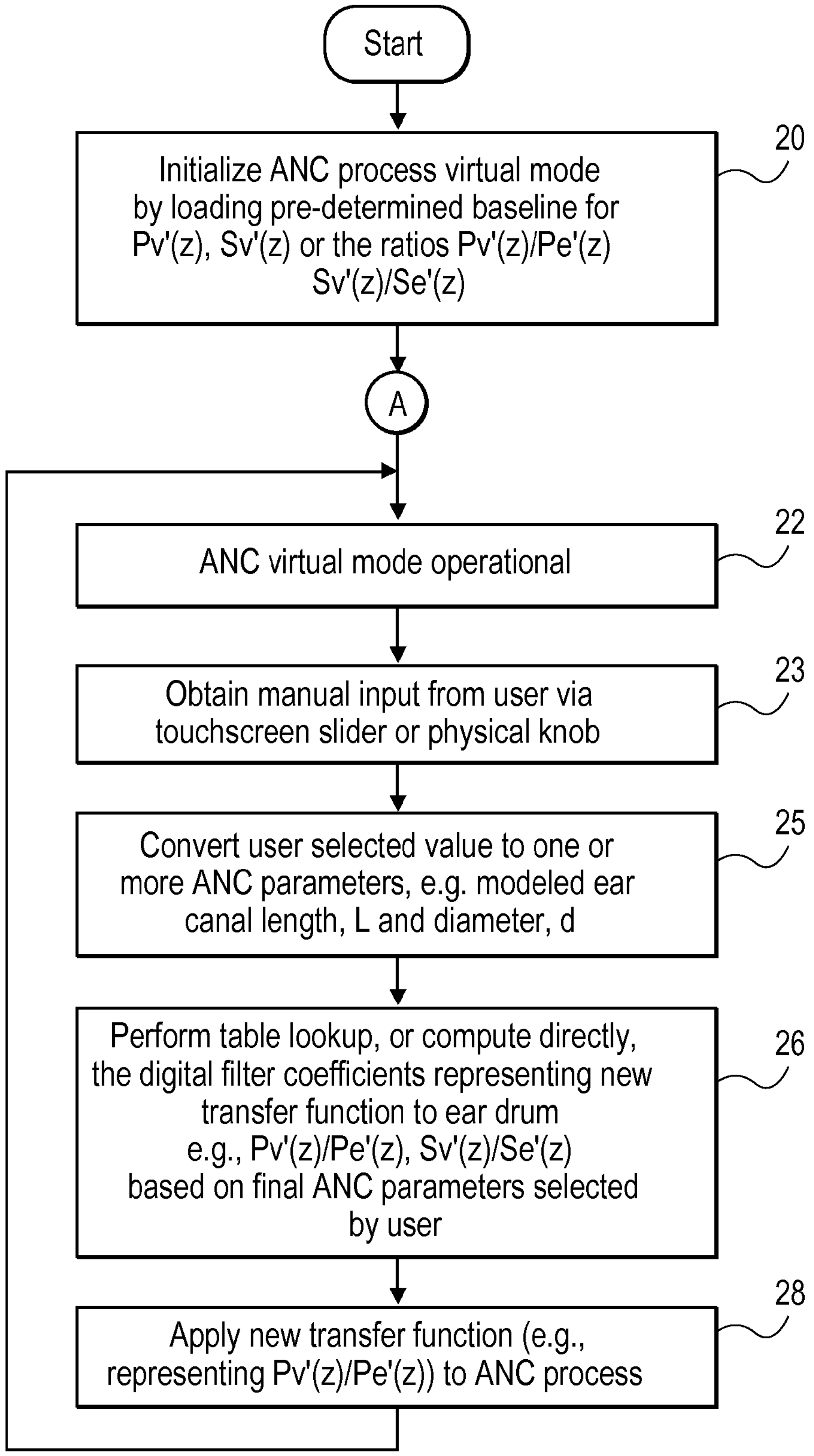
FIG. 9 depicts a process flow of a method for active noise control in a personal listening device.

A similar procedure may be followed to either experimentally measure or compute from a mathematical ear model the input impedance of the modeled ear canal as a function of changing diameter, d, of the ear canal. An example of such input impedance curves is shown in FIG. 9. Next, the computed or measured impedance curve is used to compute the transfer function to eardrum Cvm(z) or Pv'(z)/Pe'(z), as shown in FIG. 9. Once again, although magnitude v. frequency variation is shown in FIG. 9, a similar approach should be followed to compute or measure phase v. frequency variation for both the input impedance and the transfer function to eardrum.

The above described ear canal acoustic input impedance functions, and associated transfer functions Sv' and Pv', or just Cvm(z) in some cases, can be stored in the ANC controller 1, to be available for online use during a virtual error sensing mode of operation. As suggested above, they can be stored in the form of formulas and/or look up tables. Referring to FIG. 1 and to process flow diagram of FIG. 9, the ANC controller 1 and the subjective tuning module 12 can perform the following procedures, to in effect move the point at which cancellation occurs between the ant-noise and the ambient noise or disturbance, from the actual error sensor and closer to the user's ear drum. As seen in FIG. 9, the process may begin with block 20 in which the ANC controller 1 initializes its virtual sensing mode of operation, by loading a pre-determined (and stored in the ANC controller) baseline or generic version of Pv' and Sv', Cvm=Pv'/Pe', or Sv'/Se'. ANC virtual mode can then become operational while the user is wearing the head worn device of the personal listening system (block 22). Operation then continues with block 23.

In block 23, while there is some external noise that can otherwise be heard by the user (either ambient or background noise or a test sound) and the anti-noise signal is being converted to sound through the speaker 9, the personal listening system obtains manual input from, or selected by, the user, via for example a touchscreen slider (see FIG. 1) or via a physical knob (see FIG. 3). In one embodiment, the subjective tuning module 12 may be a programmed processor that is executing a user interface program that prompts the user, e.g. via text displayed on a display screen 13 as shown. Here, the display screen is part of a touch screen having a virtual slider or knob whose sweep range has been mapped to that of one or more adjustable ANC parameters. The user will manually adjust the slider, in an attempt to find the most comfortable noise cancellation setting (assuming that there is some ambient noise or other external noise or disturbance that can otherwise be heard by the user). In other words, the user here is evaluating the effects upon ANC of changing the ANC parameter. In one embodiment, each time there is a change or selection made by the user, the module 12 converts this newly selected manual user input value to a "new" ANC parameter (block 25). The ANC controller 1, then determines the new version of the virtual sensing mode transfer function Sv', Pv', Cvm, and/or Sv'/Se' that corresponds to the new ANC parameter value (block 26). Note that in a practical solution, the new transfer function in block 26 may be determined by performing a table lookup, or by direct computation of the digital filter coefficients for the digital filter that represents the transfer function. The new version of the transfer function is then applied in the adaptive filter algorithm of the ANC controller 1 (block 28).

The above process flow in blocks 22-28 may repeat as long as the user keeps changing the manual user input, until the user has finalized her choice, e.g. by touching the "Done" logo in the touchscreen embodiment or by pressing the physical knob inward for example to actuate a further switch, or by simply making no further changes to the slider. The final selection of the ANC parameter should result in better noise cancellation mainly through extended frequency range of noise cancellation.

Referring back to FIG. 1, in another subjective tuning embodiment, the module 12 plays a test sound or test tone (e.g., a single frequency or single tone, a broadband signal) through a loudspeaker 10, and that can be heard by the user while she is wearing the headphone. To ensure greatest accuracy, no other user audio content should be playing during this process. While doing so, and while the ANC controller 1 is active in virtual error sensing mode, the module 12 prompts the user to adjust a knob or slider until she is satisfied with the results (e.g., through a user interface message shown on a touch screen of the host or source device). For example, the user may be prompted to manually adjust the ANC parameter in this way until she can no longer hear the test sound; at that point, the user's subjective perception of the performance of the ANC may be deemed optimal, in that the test sound has been effectively cancelled at the user's ear drum. The user interface program may then accept this last selection of or change to the ANC parameter by the user to be final, for example when user touches the "Done." button. The so-adjusted ANC parameter may then be maintained as the ANC controller 1 continues to remain active in virtual error sensing mode.

The above-described manual adjustment sessions (that occur during ANC with virtual error sensing) may be triggered automatically, whenever for example the wired headphone or headset has been plugged in to the source device of the personal listening system, or when a wireless connection, to a wireless headset, has been established with the source device, or when the headphone or headset or cellular phone handset is being worn by the user. The user may be allowed to override and force a new adjustment session via, e.g. an audio settings option in a user interface program running in the source device.

In the subjective tuning process of FIG. 9, ANC is performed starting with a baseline or generic for the virtual error sensing mode transfer function Pv', Sv' or Cvm (which is then fine-tuned by the user). An alternative to using a previously determined baseline or generic transfer function is to compute the transfer function based on first making an actual measurement of the user's ear canal acoustic input impedance, and then using data stored in the ANC controller 1 that represents previously determined relationships between variable ear canal impedance and Cvm, to select a reliable version of Cvm. The acoustic impedance of the user's ear canal can be measured using for example the arrangement depicted in FIG. 10, in which an acoustic impedance probe circuit is added to the same personal listening system of FIG. 1 (e.g., by suitably programming a processor in the source device). An ANC method in that case can proceed according to the process flow of FIG. 11, as follows. An acoustic impedance measurement program in the personal listening device is executed that measures the acoustic input impedance of the user's ear canal, while the user is wearing a head worn device of the personal listening system (block 31). This can be performed using any conventional technique, for example one that sends out a frequency swept tone signal through the speaker 9 while simultaneously measuring sound pressure level through the error mic 7. Based on this measured input impedance, a new compensating virtual sensing mode transfer function that contains one of Pv'(z), Sv'(z), Pv'(z)/Pe'(z) and Sv'(z)/Se'(z), is determined (block 33). As suggested above, this determination can be made via a table lookup that relates a number of predetermined acoustic input impedance curves with their associated compensating virtual sensing mode transfer functions, or via a direct computation using a formula that gives for example Cvm(z) as a function of the measured ear canal acoustic input impedance. The new transfer function is then applied to an ANC process in the personal listening system, while the user is wearing the head worn device.

Figure 11:
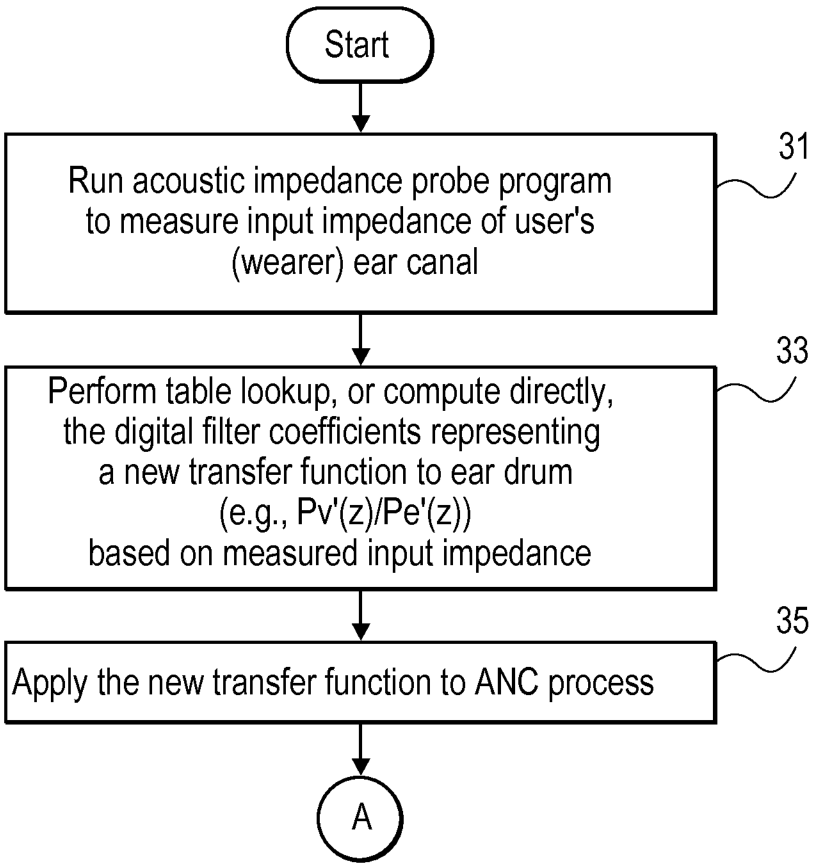
FIG. 11 is a process flow of a method for active noise control using measured acoustic input impedance of the user's ear canal.

Note that the ANC process in FIG. 11 can optionally continue with block A, where it is supplemented by tuning the new virtual mode transfer function using the subjective tuning or manual user input process of FIG. 9.

Figure 10:
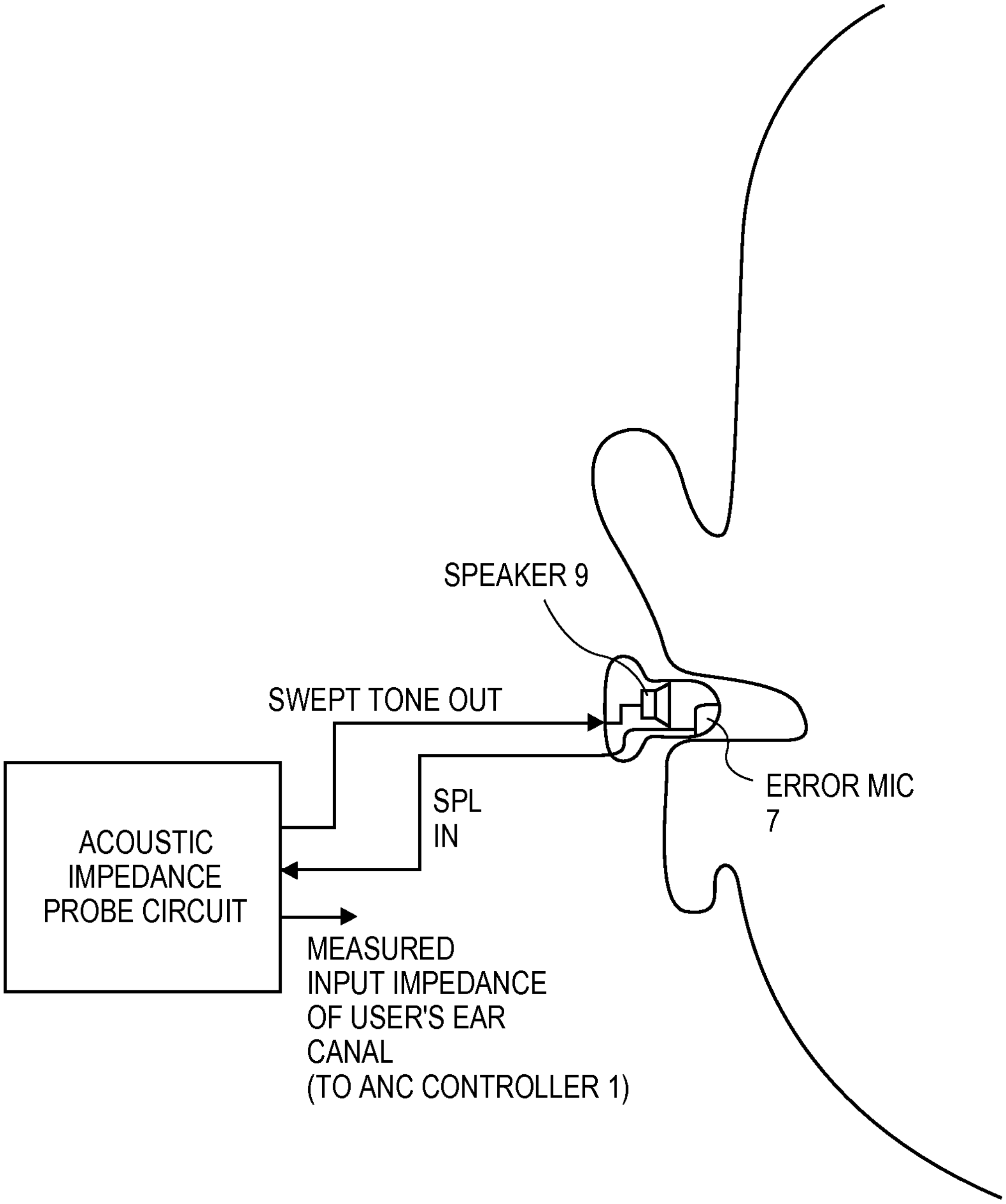
FIG. 10 depicts the measurement of acoustic input impedance of the ear canal of a user or wearer of the personal listening.

For the impedance probe approach depicted in FIG. 10, in reality there is a need here to measure both sound pressure and volume velocity produced by the speaker driver 9 (as fitted in the user's ear), to compute acoustic impedance. In this connection, it should be remembered that a very large speaker is usually considered a pressure source, while a very small speaker is usually deemed a velocity source. A velocity source would produce constant volume velocity regardless of the size of the ear canal. If the speaker driver 9 can be deemed a constant velocity source, so that the pressure it produces is directly proportional to the acoustic input impedance it sees, than in that case monitoring only the pressure (using the error mic 7) can directly yield the input impedance based on laboratory-derived knowledge of the constant volume velocity of the speaker driver 9.

Regarding the use of a slider or knob shown in FIG. 1, for purposes of capturing or obtaining a user input variable that will be mapped to the one or more ANC parameters, studies have show that shorter ear canals are also narrower, while longer ear canals are also wider. Accordingly, in one embodiment, a single scalar variable (one-dimensional slider or knob) may be sufficient to cover a useful range of ear canal dimensions, ranging from a very short and narrow canal (small L, small d) to a very long and wide canal (large L, large d). As an alternative, however, a two dimensional slider may be defined where one dimension maps to L and the other maps to d.

As indicated above, the audio signal source and the head worn audio device of the personal listening system (in which ANC with virtual error sensing is operation) may be integrated in a handset housing of a smart phone, so that the speaker 9 (see FIG. 1) is an earpiece speaker within the handset housing. Now, it may be expected that it will be more difficult to compute a reasonable generic virtual error sensing transfer function (and have it be properly adjusted online via the subjective tuning module 12), in instances where the acoustic load presented to the speaker 9 has more variability between different users and/or between different ways of wearing the head worn device, than for example the two-variable assumption made above of ear canal length and ear canal diameter. Therefore, it may be that the solutions described above are more effective for a loose fitting in-ear headphone or a tight fitting or sealing in-ear earphone, than a cellular phone handset that is being pressed against the user's ear or a supra-aural headphone. Accordingly, the solutions described above may be expected to be more suitable for virtual error sensing situations where the "unknowns" may be limited to just the ear canal dimensions, so that variations due to for example the pinna and/or concha of the users ear are not present.

An embodiment of the invention may be a machine-readable medium (such as microelectronic memory) having stored thereon instructions, which program one or more data processing components (generically referred to here as a "processor") to perform the high level digital audio processing operations described above including those of the ANC controller 1, the ANC subjective tuning module 12, and the acoustic impedance probe circuit, which may include some lower level digital signal processing including filtering, mixing, adding, inversion, comparisons, and decision making. In other embodiments, some of these operations might be performed by specific hardware components that contain hardwired logic (e.g., dedicated digital filter blocks, hardwired state machines). Those operations might alternatively be performed by any combination of programmed data processing components and fixed hardwired circuit components.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, the anti-noise signal is shown as being combined or mixed with the desired audio content and driven through the same driver. As an alternative, the desired audio content and the anti-noise may be driven through separate drivers. The description is thus to be regarded as illustrative instead of limiting.

What is claimed is:

1. A personal listening system comprising:

a head worn audio device to be worn by a user, the device having a speaker to convert an anti-noise signal into anti-noise, an error microphone and a reference microphone; and an active noise control (ANC) controller to measure an acoustic input impedance of an ear canal of the user, while the user is wearing the head worn audio device, to determine a compensating virtual sensing mode transfer function that contains one of an estimated primary path to virtual error sensor, an estimated secondary path to virtual error sensor, a ratio of the estimated primary path to virtual error sensor to an estimated primary path to actual error sensor, and a ratio of the estimated secondary path to virtual error sensor to an estimated secondary path to actual error sensor, based on the measured input impedance, and to apply the transfer function to an ANC process in the personal listening system, while the user is wearing the head worn audio device.

2. The system of claim 1 wherein the ANC controller is further to obtain manual input selected by the user while the ANC process configured with the transfer function is running;

convert the manual input selected by the user to a plurality of ANC parameters representing ear canal length and ear canal diameter;

determine a new version of said transfer function based on the plurality of ANC parameters as selected by the user; and apply the new version of the transfer function to the running ANC process.

3. The system of claim 2 further comprising a subjective tuning module that captures the manual input selected by the user.

4. The system of claim 3 wherein the subjective tuning module comprises a user interface program that when executed by a processor prompts the user, via text displayed on a display screen, to provide the manual input while listening to their desired audio content, in an attempt to find the most comfortable noise cancellation setting.

5. The system of claim 4 further comprising a touch screen of which the display screen is a part, wherein the user interface program is to produce a virtual slider or virtual knob on the touch screen for providing the manual input.

6. The system of claim 5 wherein the virtual slider is one dimensional and the subjective tuning module is programmed to map the virtual slider to the plurality of ANC parameters representing ear canal length and ear canal diameter to move the point at which cancellation occurs, between the anti-noise and ambient noise, between the error microphone and the user's ear drum.

7. The system of claim 5 wherein the virtual slider is two dimensional and the subjective tuning module is programmed to map a first dimension of the virtual slider to a first of the plurality of ANC parameters representing ear canal length, and a second dimension of the virtual slider to a second of the plurality of ANC parameters representing ear canal diameter.

8. The system of claim 3 wherein the manual input is selected by the user in response to the captured user's listening experience, so as to move the point at which cancellation occurs closer to the user's ear drum.

9. The system of claim 1 further comprising an audio signal source to produce an audio user content signal, wherein the speaker is coupled to convert the audio user content signal into user content sound.

10. The system of claim 9 wherein the audio signal source is part of a desktop computer, a smart phone, a tablet computer, a notebook computer, a wearable computing device, or a home audio video entertainment system.

11. The system of claim 9 wherein the speaker is part of an in-ear headphone.

12. An electronic device for active noise control (ANC) of a sound disturbance, with compensation for virtual error sensing, comprising:

a controller to produce an anti-noise signal in a virtual error sensing mode of operation, by performing an adaptive filter algorithm that is based on a plurality of transfer functions, wherein the controller stores a baseline version of a compensating virtual mode transfer function that contains one of a first ratio between an estimate of a primary path transfer function to a virtual error sensor and an estimate of a primary path transfer function to an actual error sensor, and a second ratio between an estimate of a secondary path transfer function to the virtual error sensor and an estimate of a secondary path transfer function to the actual error sensor, the baseline version having been determined offline in a laboratory setting, and wherein the controller is to adjust the compensating virtual mode transfer function online in accordance with manual input from a user that represents the user's listening experience of the anti-noise signal and the sound disturbance, while the controller is operating in the virtual error sensing mode.

13. The device of claim 12 wherein the controller is to compute the estimated secondary path transfer function to the actual error sensor online during the user's listening experience of the anti-noise signal.

14. The device of claim 12 wherein the controller comprises an adaptive filter controller that adapts a W filter which produces the anti-noise signal, based on 1) a version of a reference signal from a reference microphone filtered by the estimated secondary path transfer function to the virtual error sensor and 2) a difference between a) a version of the anti-noise signal filtered by the estimated secondary path transfer function to the virtual error sensor and b) a prediction of how the sound disturbance would be picked up by the virtual error sensor.

15. The device of claim 12 wherein the compensating virtual mode transfer function contains the first ratio and the controller treats the second ratio and the first ratio as equals, the controller to compute the estimated secondary path transfer function to the virtual error sensor by combining the estimated secondary path transfer function to the actual error sensor with an estimated transfer function between sound pressure at the virtual microphone and the error microphone.

16. A personal listening system comprising:

an active noise control (ANC) controller to produce an anti-noise signal that is to be converted into anti-noise by a speaker in a head worn audio device to be worn by a user, the ANC controller to use signals from error and reference microphones in the head worn audio device and a plurality of transfer functions to produce the anti-noise signal, in accordance with an adaptive filter algorithm that tries to cancel ambient noise that can be heard by the user using the anti-noise, wherein the plurality of transfer functions include an estimated primary path to actual error sensor transfer function, an estimated secondary path to actual error sensor transfer function, an estimated primary path to virtual error sensor transfer function, and an estimated secondary path to virtual error sensor transfer function, wherein a ratio of the estimated primary path to actual error sensor transfer function to the estimated primary path to virtual error sensor transfer function has a baseline which was determined offline in a laboratory setting and then stored in the system and wherein the ratio is adjusted online, while the device is being worn by the user and user content and the anti-noise are being produced by the speaker.

17. The system of claim 16 wherein in the ANC controller the ratio of the estimated primary path to actual error sensor transfer function to the estimated primary path to virtual error sensor transfer function is treated as being essentially equal to a ratio of the estimated secondary path to actual error sensor transfer function to the estimated secondary path to virtual error sensor transfer function.

18. The system of claim 17 wherein the ANC controller computes the estimated secondary path to actual error sensor transfer function online while one of test sounds and user content is being produced by the speaker.

19. The system of claim 16 wherein the adaptive filter algorithm is a least mean squares feed forward algorithm that filters a disturbance arriving at the actual error sensor.

20. A method for active noise control (ANC) in a personal listening device, comprising:

initializing an ANC process for operation in virtual error sensing mode, by loading a pre-determined generic for one of the following transfer functions, an estimated primary path to virtual error sensor transfer function, an estimated secondary path to virtual error sensor transfer function, a ratio of the estimated primary path to virtual error sensor to an estimated primary path to actual error sensor transfer function, and a ratio of the estimated secondary path to virtual error sensor to an estimated secondary path to actual error sensor transfer function;

performing the ANC process using the loaded generic transfer function;

obtaining manual input selected by a user of the personal listening device;

converting the obtained manual input to one or more ANC parameters;

determining a new version of said one of the transfer functions based on the ANC parameters selected by the user; and applying the new version of said transfer function to the ANC process being performed.

21. The method of claim 20 wherein performing the ANC process comprises:

producing an anti-noise signal, that is to be converted into anti-noise by a speaker in a head worn audio device that is worn by the user, using an adaptive filter;

filtering a reference signal in accordance with the secondary path to virtual error sensor transfer function;

filtering a residual noise signal, obtained from an error microphone in the head worn audio device, in accordance with the ratio of the estimated primary path to virtual error sensor to an estimated primary path to actual error sensor transfer function; and adjusting the adaptive filter in accordance with an adaptive filter algorithm that uses a difference between the filtered residual noise signal and a version of the anti-noise signal filtered by the secondary path to virtual error sensor transfer function.

22. The method of claim 20 wherein determining a new version of the transfer function comprises one of performing a table lookup and computing directly a plurality of digital filter coefficients of a digital filter that represents the new version of the transfer function.

23. A method for active noise control (ANC) in a personal listening device, comprising:

executing an acoustic impedance measurement program in the personal listening device that measures an acoustic input impedance of a user's ear canal, while the user is wearing a head worn device of the personal listening device; determining a compensating virtual sensing mode transfer function that contains one of an estimated primary path to virtual error sensor, an estimated secondary path to virtual error sensor, a ratio of the estimated primary path to virtual error sensor to an estimated primary path to actual error sensor, and a ratio of the estimated secondary path to virtual error sensor to an estimated secondary path to actual error sensor, based on the measured input impedance; and applying the transfer function to an ANC process in the personal listening device, while the user is wearing the head worn device.

24. The method of claim 23 further comprising:

obtaining manual input selected by the user while the ANC process configured with the transfer function is running;

converting the manual input selected by the user to a plurality of ANC parameters representing ear canal length and ear canal diameter;

determining a new version of said transfer function based on the ANC parameters as selected by the user; and applying the new version of the transfer function to the running ANC process.

* * * * *